US00PP27248P3

(12) United States Plant Patent
Bradford et al.

(10) Patent No.: US PP27,248 P3
(45) Date of Patent: Oct. 11, 2016

(54) CHERRY TREE NAMED 'GLENHEART'

(50) Latin Name: *Prunus avium*
Varietal Denomination: Glenheart

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 101 days.

(21) Appl. No.: 14/544,247

(22) Filed: Dec. 15, 2014

(65) Prior Publication Data

US 2016/0174433 P1 Jun. 16, 2016

(51) Int. Cl.
*A01H 5/08* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

| | | | | |
|---|---|---|---|---|
| PP12,859 | P2 | 8/2002 | Bradford | |
| PP22,603 | P2 * | 3/2012 | Zaiger et al. | Plt./181 |
| PP22,950 | P2 * | 8/2012 | Zaiger et al. | Plt./181 |
| PP26,315 | P3 * | 1/2016 | Bradford et al. | Plt./181 |

* cited by examiner

*Primary Examiner* — June Hwu

(57) ABSTRACT

The present invention relates to a cherry tree, *Prunus avium*, and more particularly to a new and distinct variety broadly characterized by a medium to large size, vigorous, hardy, self-unfruitful, productive and regular bearing tree. The fruit matures under the ecological conditions described in mid May, with first picking on May 12, 2014. The fruit is uniformly medium to large in size, excellent in flavor with 22 to 26 brix, somewhat oblate in shape, clingstone in type, heat tolerant, very firm in texture, dark red in flesh color, dark red in skin color, and is strongly attached to a short stem.

1 Drawing Sheet

Botanical classification: *Prunus avium.*
Varietal denomination: 'GLENHEART'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Glenheart'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2002 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label "Glenred House". They were grown as seedlings on their own root in our greenhouse, and upon reaching dormancy transplanted to a cultivated area of our experimental orchard located near Le Grand, Calif. in Merced County (San Joaquin Valley). During the summer of 2008 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (unpatented) rootstock, upon which the present variety was compatible and true to type.

The present variety of cherry tree is most similar to its seed parent, 'Glenred' (U.S. Plant Pat. No. 12,859) cherry, by being self-unfruitful, by having reniform glands, by being productive, and by producing fruit that is dark red in skin color, red in flesh color, somewhat oblate in shape, sweet, and fairly crack resistant, but is distinguished therefrom by blooming about four days later, by having the ability to carry and size a heavy crop that stays firm on the tree for a longer period of time, and by producing cherries that are somewhat larger in size, that are clingstone instead of semi-freestone, that are more heat tolerant, that ripen about four days later, and that have a shorter stem that is more strongly attached to the fruit.

The present variety of cherry tree is similar to 'El Capitan' (U.S. Plant Pat. No. 26,315) cherry, by being self-unfruitful, by having reniform glands, by being productive, and by producing fruit that has a short stem and that is dark red in skin color, almost full red in flesh color, somewhat oblate in shape, clingstone in type, and very sweet in flavor, but is distinguished therefrom by blooming about six days earlier, by producing cherries that are somewhat larger in size, and that ripen about six days earlier.

The present variety of cherry tree is similar to 'Royal Brynn' (U.S. Plant Pat. No. 22,950) cherry, by being self-unfruitful, by blooming in mid March, by having reniform glands, by being productive, and by producing fruit that is full red in skin color, almost full red in flesh color, and clingstone in type, but is distinguished therefrom by producing cherries that have a shorter stem and that are somewhat smaller in size, that are sweeter in flavor, and that ripen about eleven days earlier.

The present variety of cherry tree is similar to 'Royal Elaine' (U.S. Plant Pat. No. 22,603) cherry, by being self-unfruitful, by blooming in mid March, by having reniform glands, by being productive, and by producing fruit that is full red in skin color, almost full red in flesh color, and clingstone in type, but is distinguished therefrom by producing cherries that have a shorter stem and that are smaller in size, that are sweeter in flavor, and that ripen about ten days earlier.

SUMMARY OF VARIETY

In summary, the present variety is characterized by a medium to large size, vigorous, hardy, self-unfruitful, productive and regular bearing tree. The fruit matures under the ecological conditions described in mid May, with first picking on May 12, 2014. The fruit is uniformly medium to large in size, excellent in flavor with 22 to 26 brix, somewhat oblate in shape, clingstone in type, heat tolerant, very firm in texture, dark red in flesh color, dark red in skin color, and is strongly attached to a short stem.

DRAWING

The accompanying photograph displays four fruits with the stems attached to exhibit the skin color and form, two half fruits sectioned to reveal the flesh and fibers, two individual stones, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 16, 2014, on the original tree during its twelfth growing season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Glenred' cherry (U.S. Plant Pat. No. 12,859).
Pollen parent: Unknown.

TREE

Size: Medium to large, maintained to a height of 14' [4.27 m.] and a spread of 8' [2.44 m.] after twelve growing seasons utilizing typical pruning.

Vigor: Vigorous, responding typically to irrigation and fertilization. The plant should be grown on a standard commercial rootstock for production purposes.

Growth: Spreading and dense.

Form: Central leader.

Hardiness: Hardy with respect to central California winters. Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-unfruitful, must be cross pollinated by another early to mid seasonal blooming cherry variety, such as 'Glenred' (U.S. Plant Pat. No. 12,859).

Bearing: Regular bearer, with no crop failures observed.

Trunk:

*Size*.—Medium, reaching a maximum diameter of 5" [127 mm.] after the twelfth growing season.

*Texture*.—Medium shaggy.

*Bark color*.—A Dark grayish yellowish brown [81. d.gy.yBr] and Dark brown [59. d.Br] variegation.

*Lenticels*.—Approximate Number Per Square Inch: 9. Color: Strong yellowish brown [74. s.yBr]. Size: ⅛" [3.2 mm.] to ⅜" [9.5 mm.] in length. Width is typically one fourth as much as the length. Shape: Eye-shaped, elongated.

Branches:

*Size*.—Diameter of main scaffold measured 12" above the first hanger is 3½" [88.9 mm.].

*Texture*.—Smooth on first and second year wood, increasing roughness with age.

*Color*.—1st Year Wood topside: Light grayish red [18. l.gy.R]. 1st Year Wood underside: Brilliant yellow green [116. brill.YG]. 2nd Year Wood: Strong brown [55. s.Br]. 3rd Year Wood: Deep yellowish brown [75. deep yBr].

*Lenticels*.—Number Per Square Inch: About 32 on second year wood. Color: Moderate orange yellow [71. m.OY]. Size: Small with an average length of ⅛" [3.2 mm.] and average width of 1/32" [0.8 mm.] on second year wood. Shape: Rectangular, elongated.

Leaves:

*Size*.—Medium. Average Length: 5" [127 mm.]. Average Width: 2¼" [57.2 mm.].

*Arrangement*.—Alternate.

*Thickness*.—Medium.

*Form*.—Elliptical.

*Apex*.—Acuminate.

*Base*.—Acute to rounded.

*Surface*.—Smooth.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Pale yellow green [121. p.YG].

*Petiole*.—Average Length: 1¼" [31.8 mm.]. Average Thickness: 1/16" [1.6 mm.]. Color: Grayish red [19. gy.R] on the topside, Strong yellow green [117. s.YG] underneath.

*Stipules*.—Number: 2 per leaf at development stage. Average Length: ⅜" [9.5 mm.]. Color: Moderate yellow green [120. m.YG] becoming Moderate olive green [125. m.OlG ] with age.

*Glands*.—Number: Mostly 2 per leaf. Position: Usually alternately positioned on the petiole with only a few opposite. Size: Medium, about 1/32" [0.8 mm.] in length. Form: Reniform to slightly oval shape. Color: Deep yellow green [118. deep YG] toward the edges, Grayish red [19. gy.R] toward the center.

*Leaf buds*.—Pointed, medium.

Flower buds:

*Hardiness*.—Hardy, with respect to central California winters.

*Diameter*.—Typically 5/16" [7.9 mm.] 3 days before bloom.

*Length*.—Typically 5/8" [15.9 mm.] 3 days before bloom.

*Form*.—Free, not touching.

*Surface*.—Non-pubescent.

*Tip color*.—White [263. White].

Flowers: Perfect, complete, perigynous, usually a single pistil, typically about twenty stamens, five sepals and petal locations alternately positioned.

*Average flower diameter*.—1 7/16" [36.5 mm.].

*Average flower depth*.—1/2" [12.7 mm.] when fully open.

*Number of petals*.—Usually five, extra petals or fragments are rarely observed.

*Petal arrangement*.—Overlapping.

*Petal shape*.—Circular to slightly oval.

*Petal margin*.—Smooth to slightly wavy.

*Average petal diameter*.—11/16" [17.5 mm.]

*Average petal length*.—11/16" [17.5 mm.].

*Petal apex*.—Rounded.

*Petal base*.—Rounded to slightly cuneate.

*Petal color*.—White [263. White] on both sides.

*Anther color*.—Light yellow [86. l.Y].

*Pollen*.—Anthers produce a moderate amount of Brilliant yellow [83. brill.Y] pollen.

*Stigma color*.—Brilliant greenish yellow [98. brill.gY].

*Stigma position*.—Typically located about even with the nearby anthers.

*Ovary*.—Non-pubescent.

*Sepal color*.—Deep yellowish pink [30. d.yPk] over Vivid greenish yellow [97. v.gY] on the outer surface. The inner surface is Pale yellow green [121. p.YG].

*Sepal outer surface*.—Pubescent.

*Sepal length*.—5/16" [7.9 mm.].

*Sepal width*.—3/16" [4.8 mm.].

*Sepal apex*.—Elliptical to match the sepal length and width.

*Sepal margin*.—Fairly smooth.

*Average pistil length*.—11/16" [17.5 mm.].

*Average stamen length*.—9/16" [14.3 mm.].

*Fragrance*.—Moderate.

*Bloom density*.—Heavy.

*Blooming period*.—Early to medium, blooms four days after 'Glenred' (U.S. Plant Pat. No. 12,859).

*Onset of bloom*.—One percent on Mar. 12, 2014.

*Date of full bloom*.—Mar. 26, 2014.

*Duration of bloom*.—One to two weeks, dependent on ambient temperature.

*Number per cluster*.—Usually 2 to 9, 5 average.

FRUIT

Maturity when described: Firm ripe, May 16, 2014.

Date of first picking: May 12, 2014.

Date of last picking: May 22, 2014.

Size: Uniform, medium to large.

*Average diameter axially*.—1" [25.4 mm.].

*Average diameter across cheek plane*.—1 3/16" [30.2 mm.].

*Average diameter across suture plane*.—1" [25.4 mm.].

*Typical weight*.—0.42 ounces [12 grams].

Form: Uniform, symmetrical, somewhat oblate, compressed axially and around the suture.

*Axial view form*.—Elliptical to round.

*Suture plane form*.—Oval to round.

*Cheek plane form*.—Mostly oblate.

Suture: An inconspicuous line located in a shallow trough, extending from the base to the pistil point.

Ventral surface: Cordate, lipped slightly toward the apex.

Lips: Mostly equal.

Cavity: Flaring, circular, suture showing on one side.

*Depth*.—1/8" [3.2 mm.].

*Breadth*.—1/2" [12.7 mm.].

Base: Somewhat cordate if viewed parallel to the suture plane.

Apex: Cordate.

Pistil point: A Light yellowish brown [76. l.yBr] inconspicuous dot.

Stem: Short.

*Average length*.—1 1/8" [28.6 mm.].

*Average width*.—1/16" [1.6 mm.].

*Attachment*.—Very strong.

Skin:

*Thickness*.—Medium.

*Surface*.—Smooth.

*Tenacity*.—Tenacious to the flesh.

*Astringency*.—Slight.

*Tendency to crack*.—None observed in dry seasons, fairly resistant to cracking in wet season.

*Color*.—Blackish red [21. blackish R] over a Very deep red [14. v.deep R] background.

Flesh:

*Color*.—Dark red [16. d.R] near the skin and Very deep red [14. v.deep R] near the stone.

*Surface of pit cavity*.—Covered with Very deep red [14. v.deep R] broken fibers when twisted away from the stone.

*Amygdalin*.—Moderate.

*Juice*.—Abundant, rich.

*Juice color*.—Very deep red [14. v.deep R].

*Texture*.—Firm, crisp, meaty.

*Fibers*.—Abundant, fine, tough.

*Ripens*.—Mostly even, slightly earlier at the apex.

*Heat tolerance*.—Observed to remain firm during extended periods of heat prior to and during the harvest season.

*Flavor*.—A nice balance of acid and sugar, typically 22 to 26 brix.

*Aroma*.—Slight.

*Eating quality*.—Excellent.

STONE

Type: Clingstone.
Form: Oval.
Hilum: Narrow, oval.
Base: Rounded.
Apex: Rounded.
Sides: Equal.
Surface: Fairly smooth.
External color of stone: Light grayish yellowish brown [79. l.gy.yBr] when first removed.
Pit wall color when cracked: Pale yellow green [121. p.YG].
Cavity surface color: Pale yellow green [121. p.YG].
Average pit wall thickness: 3/64" [1.2 mm.]
Average width: 3/8" [9.5 mm.].
Average length: 7/16" [11.1 mm.].
Average breadth: 5/16" [7.9 mm.].
Tendency to split: None observed in dry season.
Kernel:

*Form*.—Oval.
*Skin color*.—Pale yellow [89. p.Y] when first removed.
*Pellicle color*.—Grayish yellow [90. gy.Y].
*Vein color*.—Grayish yellow [90. gy.Y].
*Apex tip color*.—Dark grayish yellow [91. d.gy.Y] when first removed.
*Taste*.—Bitter.
*Viable*.—Yes.
*Average width*.—3/16" [4.8 mm.].
*Average length*.—5/16" [7.9 mm.].
*Amygdalin*.—Abundant.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to its seed parent, 'Glenred' (U.S. Plant Pat. No. 12,859) cherry, by being self-unfruitful, by having reniform glands, by being productive, and by producing fruit that is dark red in skin color, red in flesh color, somewhat oblate in shape, sweet, and fairly crack resistant, but is distinguished therefrom by blooming about four days later, by having the ability to carry and size a heavy crop that stays firm on the tree for a longer period of time, and by producing cherries that are somewhat larger in size, that are clingstone instead of semi-freestone, that are more heat tolerant, that ripen about four days later, and that have a shorter stem that is more strongly attached to the fruit.

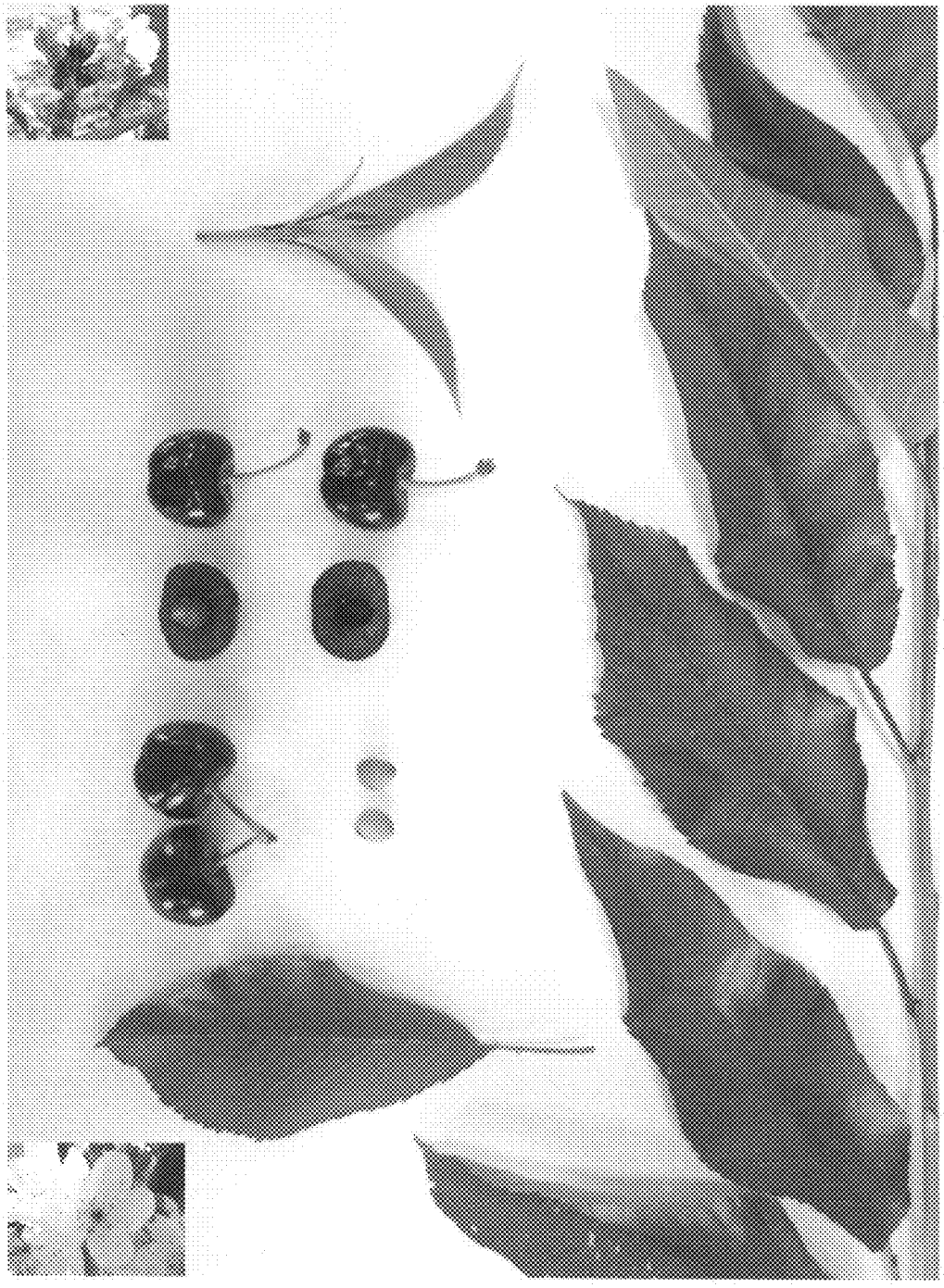

* * * * *